United States Patent [19]

Nagase et al.

[11] Patent Number: 4,962,043
[45] Date of Patent: Oct. 9, 1990

[54] SIMPLIFIED DETECTION IMPLEMENT

[75] Inventors: Moriharu Nagase, Ebina; Mutsumi Shibuya, Yokohama; Kuniaki Asami, Tokyo; Katsuo Matsumoto, Furukawa; Hikaru Teranishi, Iwadeyama; Sukeo Saito, Yokohama, all of Japan

[73] Assignees: Showa Yakuhin Kako Co., Ltd, Tokyo; Nitto Electric Industrial Co., Ltd., Osaka, both of Japan

[21] Appl. No.: 332,621

[22] Filed: Apr. 3, 1989

Related U.S. Application Data

[63] Continuation of Ser. No. 53,148, May 21, 1987, abandoned, which is a continuation of Ser. No. 682,263, Dec. 17, 1984, abandoned.

[30] Foreign Application Priority Data

Dec. 20, 1983 [JP] Japan ................. 58-240653

[51] Int. Cl.$^5$ ............................................. G01N 1/28
[52] U.S. Cl. .................... 436/165; 422/57; 422/58; 435/805; 436/2; 436/147; 436/166; 436/169; 436/170; 436/808
[58] Field of Search ................. 422/56, 57, 58; 435/805; 436/2, 147, 165, 166, 169, 170, 807, 808

[56] References Cited

U.S. PATENT DOCUMENTS

| 3,367,841 | 2/1968 | Buissiere et al. | 422/56 |
| 3,996,006 | 12/1976 | Pagano | 422/58 |
| 4,076,502 | 2/1978 | Dugle et al. | 422/58 |
| 4,420,353 | 12/1983 | Levine | 422/56 |
| 4,448,548 | 5/1984 | Foley | 422/58 |
| 4,472,353 | 9/1984 | Moore | 422/56 |

FOREIGN PATENT DOCUMENTS 58-225029 12/1983 Japan .

Primary Examiner—Kenneth M. Schor
Assistant Examiner—Lori Ann Johnson
Attorney, Agent, or Firm—Bucknam and Archer

[57] ABSTRACT

A simplified detection implement for use in the biological or chemical tests such as medical, pharmaceutical, microbiological, enzymological or analytical tests comprising an adhesive sheet (1) having an adhesion material layer (4), the adhesion sheet (1) also having an area "a" in an optimal shape and an area "b" in an optimal shape with a folding line (6) at the border of areas "a" and "b"; a small test material (3) adhered to the adhesion material layer (4) and being placed approximately at the center of area "a" of the adhesive sheet (1); and a peelable protection sheet (2) covering the surface of the adhesion material layer (4) and having an opening (5) big enough to expose the whole surface of the small test material (3) as well as being so positioned to expose the small test material (3) when areas "a" and "b" are overlapped by folding the adhesive sheet (1) at the folding line (6), and when areas "a" and "b" being overlapped the majority or part of area "a" of the adhesive sheet (1) acts as the adhesive portion to a heating apparatus or heated body after the small test material (3) being such as added with reagent for detection, the small test material (3) being such as small test paper and being incorporated with substance to be tested therein or thereon at the time of testing.

7 Claims, 5 Drawing Sheets

FIG. 1A
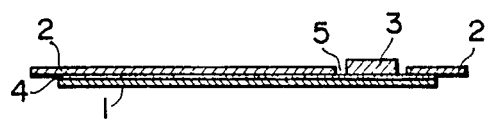
FIG. 1B
FIG. 2
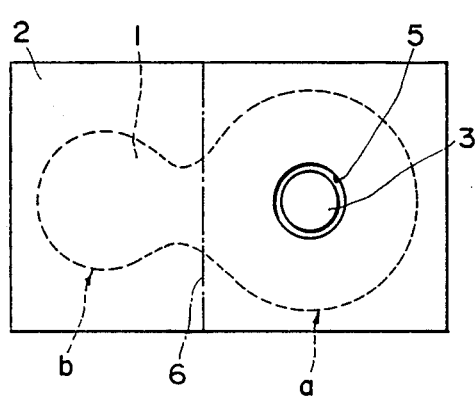
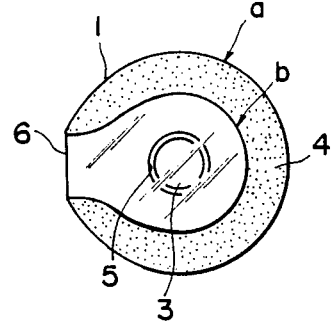
FIG. 3
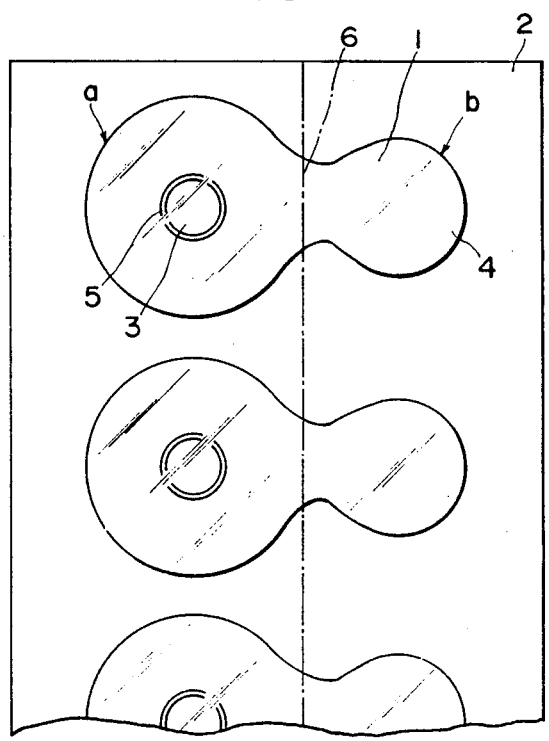

SIMPLIFIED DETECTION IMPLEMENT

This is a continuation of application Ser. No. 053,148, filed May 21, 1987, and now abandoned which was a continuation of U.S. Ser. No. 682,263 filed on Dec. 17, 1984 and now abandoned.

BACKGROUND OF THE INVENTION

This invention is in relation to a simplified detection implement for the biological or chemical tests of the substance to be subjected for inspection, e.g. the medical, pharmaceutical, microbiological, enzymological or analytical tests.

The various tests above are medically, physical checkup, clinical tests of patients and chemically, miniturizing the various food, pharmacentical, mineral, animal and plant samples collected to simplify their storage or determine a test by letting them react to a detection reagent on the spot. The principle of these various tests are basically, chemical reactions which generally indicate better reactivity when heated and in many cases the conditions of reaction around 20° C., 35° C., 80° C. and boiling point are defined Needless to say, as it is better to be able to attain the intended reaction at the lowest temperature possible, contrivances are made on the reaction system, reagent, or reaction accelerator and also achieve the desired test by the combination with some detection device, but in most cases, when heated at around 35° C. a speedy test is generally possible without accompanying any side reaction or deteriorating the sensitivity of the reaction. It is ideal, that all items or the majority such as collection, holding storage, reaction, testing and preservation of test results concerning the subject to be tested is carried out by the use of the same implements and many of the various types of implements have already been devised accordingly and put into practical use. Of course, there are economical reasons but simplicity accuracy and small in cubic volume and other advantages are recognized in the existing implements. Also, mainly in ,medical chemistry it is important to guarantee safety to the subject of the test as well as the operator at time of using the implement.

SUMMARY OF THE INVENTION

The detection implement of this invention is a further improvement made on the detection implement of prior art, to which all or a portion of the reaction system in the test is soaked into the porous small substance in advance and further this small material is adhered in a dry state to a high molecular film that has a sticky surface and said sticky surface of this film is protected by a protection sheet, to which an opening is made in advance and as sad opening is made a little bigger than the small substance, said small substance penetrates the opening to be exposed and the adhesive surface of the film serves also another purpose to be adhered to a heated body or heating apparatus in order to maintain reaction temperature.

BRIEF DESCRIPTION OF THE DRAWINGS

The attached drawings are examples of the detection implement of this invention and FIG. 1A is a cross-sectional view and
FIG. 1B is a plane view;
FIG. 2 shows the state just before the detection implement is adhered to the heating apparatus with the middle section of the adhesive sheet folded and laid over the other after the protection sheet is peeled off from the detection implement in order to submit said detection implement for detection.

FIG. 3 shows the serially linked type of the detection implement.

FIG. 5 shows the examples of the serially linked;

DESCRIPTION OF THE INVENTION

Figure 4:
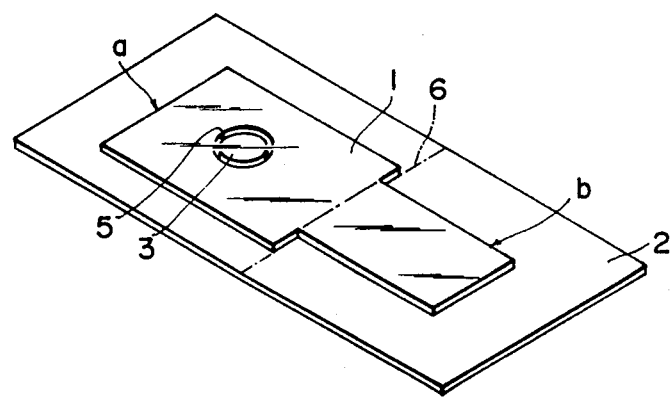
FIG. 4 and 5 show the other shape (Square shape) of the detection implement of this invention.

The detection implement of this invention is composed of an adhesive sheet 1 which can be peeled off, a protection sheet 2 and a small test material 3 which is used for the purpose of detecting the substance to be tested, and said three portions are laid one upon another forming a stack layer, and said three portions can all be transparent or any one of them by opaque option or a part or all of them be administered with a transparent or opaque printing. The inner surface of the adhesive sheet 1 is partly or a wolly plastered with the adhesion material 4 and approximately to the center or a little either to the left or right of the center position a small test material 3 is adhered and the protruding portion around the rim of area "a" of said adhered surface will be the part to stick to the heating apparatus or heated body.

The protection sheet 2 is a thin sheet that is large enough to cover up the adhesion material layer 4 of the adhesive sheet 1 or a bit larger and in conformity with the shape of the small test material 3, an opening of a little larger shape is cut off or pierced, thus rendering the small test material 3 to penetrate the separation sheet 2. The adhesive sheet 1 is generally transparent, and when this sheet 1, to which the small test material is adhered, is folded at the folding line 6 by having the surface of the adhesion material layer 4 from the inner surface, thus rendering it to stick as if to cover over the small test material 3, the adhering sheet covering over the small test material 3 makes a desirable partner by being smaller shape and around the rim of said adhesive sheet the peripheral part of area "a" of the adhesive sheet 1 to which the small test material 3 is adhered is exposed and this exposed region will stick to the heated body or heating apparatus.

The small test material 3 is an inorganic or organic porous substance and it is more convenient that it be a small piece of paper. The reagent for the test is generally soaked into the small test material in advance but depending on the purpose of use, there are cases where it is not soaked in advance.

Figure 5:
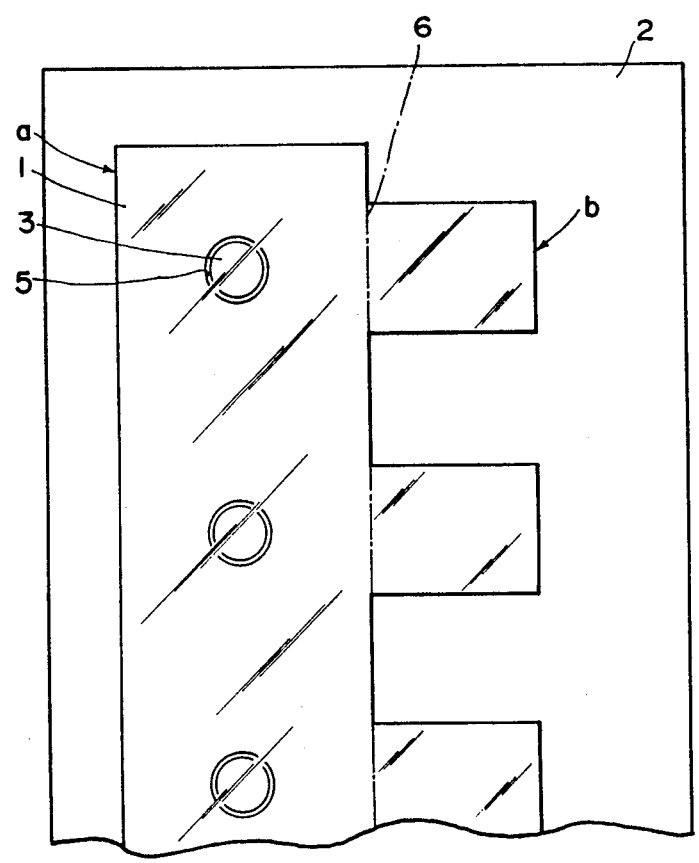
Figure 6:
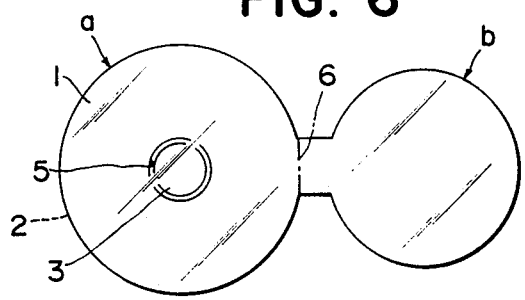
FIGS. 6–8 show the protection sheet 2 and adhesive sheet 1 in the same shape and size, FIG. 6 in round shape, FIG. 7 in square, FIG. 8 in serially linked.
Figure 7:
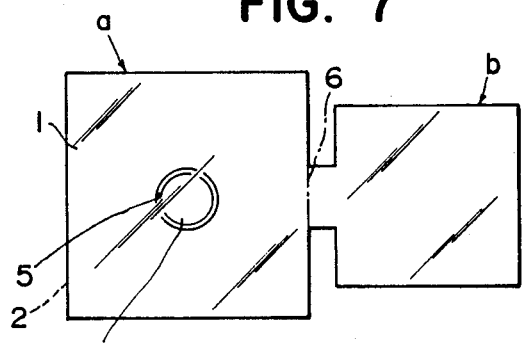
Figure 8:
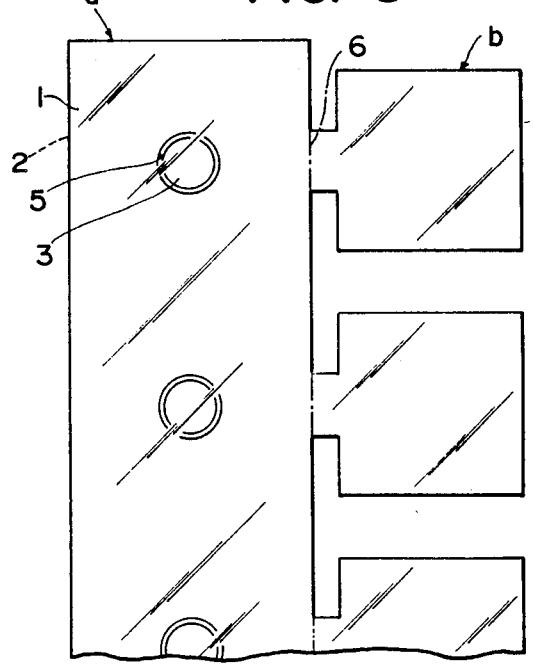

The adhesive sheet 1, illustrated in FIG. 1–3, is of a horseshoe, scallop inverted jar or balloon shape, but the adhesive sheets 1 in FIGS. 4–5 show a convex shape and when folded, will take a square shape. Thus, selection of the shape of the adhesive sheet 1 is optional. The shape of area "a" and "b" are also optional, as they could be any of a round, oval or polygon shape or combinations of them.

The detection implement of this invention is of singular shape or sold and used in plural shapes. The plural shapes may well be serially linked (FIGS. 5-8) which are used in group examinations.

One example of a concrete form of this invention is that the adhesive sheet 1 is a thin, soft film of polyvinyl chloride, polyvinylidene chloride, polyethelene or polypropylene, etc., but as a film sheet the "a" area to the right and the "b" area to the left of the folding line in FIG. 1B 3 may both be or may not be from the same sheet, and in some cases where they are not from the same, the quality and/or thickness of the film may differ. Namely, the film of area "a" may be of firm and stiff quality such as that of rigid polyvinyl chloride, polyester, polyethylene telephthalate, etc. In this case, it is desirous that the "b" area be of a soft and thin film and as desirable partner the area of "b" should be a little smaller than that of "a". The adhesion material 4 is applied entirely, dottedly or linearly on the surface of areas "a" and "b" and in some cases the component and the applied shape of the adhesive may differ.

Protection sheet 2 is ordinarily made of paper applied with a silicone film on one side and the surface of this side is pressed against the adhesion material layer 4 to cover up its entire area so as to protect the surface of said adhesion material.

The protection sheet is penetrated by a small test material 3 and an opening is made to expose it. Said small test material 3 is fixed on to area "a" and does not come in contact with the protection sheet.

In this invention, it is a very important condition that the protection sheet 2 does not come into contact with the small test material 3. When the subject to be tested, namely, a chemical reagent, an animal, plant or mineral liquid, a culture liquid of bacteria, saliva, milk, etc., is to be inoculated to the small test material 3, in order to render it possible to executed the inoculation even with the protection sheet sticking unpeeled, it is more amenable to the operation of the adhesion material 4 were not exposed. Also, in case there are no opening in the protection sheet 2, in other words, when the state of the stack layer between the adhesion material layer 4 and protection sheet 2 and where the small test material 3 is sandwiched form a stack layer, trace amount of the component vaporizing from said adhesion material might produce bad effect on the composition of the reagent. But, there are no such apprehensions in this invention.

When putting the detection implement of this invention into a product form, the raw materials of both the adhesive sheet 1 and protection sheet 2 are long rolls of film, which are respectively supplied separately to the processing machine, but according to this invention, and after an opening where the small test material to be placed is punctured at a fixed position and at regular intervals, this protection sheet with the opening is pasted together with the adhesive sheet 1. In this case, at the portion of the opening of said protection sheet 2, the adhesion material 4 is exposed, so the small test material 3 is adhered and fixed to this exposed adhesive area. If, by way of experiment, we assume that one small test material 3 is adhered and fixed at a desired place on the surface of the adhesion material layer 4 of the adhesive sheet 1, the small test material must, one by one, be adhered accurately and at a speed sufficient to satisfy the need of industry, and the precision required is many times higher than that of this invention and it is not difficult to image how hard it will be to industrialize production of such detection implement based on this assumption.

Contrary to this, with regard to the detection implement of this invention, all that is necessary is to drop a piece of test material into the opening of the protection sheet mentions heretofore, which renders industrialization much simple and efficient.

The simplified detection implement thus obtained, can, for instance, be packed tightsealed in a metal laminated film in fixed numbers and supplied to the consumer The consumer, namely, the test operation, will, for instance, at time of using, immediately peel off the protection sheet 2, after seeping the saliva to be tested into the small test material 3 of this detection implement, and will fold the adhesion sheet at the folding line 6 with the adhesive facet facing inward, thus rendering the inner facet (areas "a" and "b" of (1)) come into close adhesion. At this point, the exposed adhesive area that have occurred, due to the difference of area size between "a" and "b", will be adhered to a heated body, which is heated to around 35° C., hence, the test operation can, in a short period of 15 minutes or so, read the changes of color of the test piece and for instance, determine the number of living bacteria. The heated body used with the purpose to facilitate the reaction is only required to be a substance of constant temperature that will facilitate the reaction of the cells of the living bacteria to the reagent, like for instance, good results are obtainable just by directly adhering on the human skin. On the other hand, as the test materials are held between adhesive sheets and under such state of being intercepted from the atmosphere and also heated in a state eliminating the risk of scattering, the living bacteria, it is placed constantly under a fixed reaction environment, reproduceable results are obtainable. Thus, the simplified detection implement of this invention will not require any special apparatus even in the case of group examination of school children and it not only is convenient and enables attainment of the objective of the examination in a short time but industrial production can be conducted easily and efficiently.

As a heating apparatus or heated body an incubator may well be utilized, and for instance, a metal surface, glass surface, a container with warm water heated by wolfram filament bulb, an infrared lamp or it could even be the surface of the skin of human beings.

EXAMPLE 1

Hereunder, is an example where the detection implement of this invention is utilized as the dental caries activity testing apparatus for the diagnosis of the caries.

The inventors have, in the papers under Japanese patent application 57-106389 (1982) disclosed a simple discrimination method of dental caries and in implement thereof. The gist of the invention is that, in the prior invention, a sample liquid containing cariogenous microorganisms, for instance, a fixed amount of saliva is dripped on to a dried small test material seeped with a certain reagent ingredient liquid, and it is heaped up and covered over tightly at the central part of two transparent adhesive sheets then by storing it and keeping it at a constant temperature of 37° C. for at least 15 minutes, the degree of the cariogenous microorganism contained in the saliva can be seen by the corresponding degree of change in color on the small test material, which is a simple method and apparatus to determine the progress of caries.

In this preceding invention, the component of the reagents were composed of resazurin, triphenyl tetrazorium, neotetrasorium, 2.6-dichlorphenol indophenol or methylorange or 0.05-0.003 weight % of their salts and 10 weight % of sucrose.

The reagent component used in this example of this invention were resazurin 0.05% and sucrose 10% and after soaking a hard and round filtration paper of 0.8 mm in thickness and 8 mm in. diameter into this solution it was dried and used as the small testing material.

The protection sheet is a brown oval 50 mm×110 mm shaped kraft paper and the surface to come into contact with the adhesive material was coated with a silicone resin and an opening of 9 mm in diameter was made at the spot corresponding to approximately the center of area "a" of the adhesive sheet. The dimensions of the adhesive sheet were 45 mm in diameter at the "a" area, 30 mm at the "b" area and the adhesive sheet and protection sheet were adhered tightly so that the approximate center of area "a" of the adhesive sheet will tally with the opening made in the protection sheet. To the surface of the adhesion material (9 mm in diameter) of the adhesive sheet which is exposed from the opening in the protection sheet, the small test material prepared above is plastered on and fixed. Furthermore, the adhesive sheet 1 is of polyvinyl chloride of 20 mm thickness and the area "a" in FIG. 1B is totally painted white and area "b" is transparent.

The test operator will collect one drop of human saliva and drip it on to the small test material 3 and immediately peel off the protection sheet 2 and fold the "b" area (FIG. 1B) of the adhesive sheet at the folding line 6 with the adhesive material facet on the inside and cover the small test material with the "b" area of the adhesive sheet under such state of removing as much of the atmosphere possible and after tightly adhering area "b" to "a", a horseshoe or inversed "U" shaped adhesive facet of about 7 mm width will be exposed around the "a" area (FIG. 2). Place on and adhere this adhesive facet immediately to a heated body i.e. the inner part of the upper arm of a human being. By holding it for about 15 minutes the color of the small test material will undergo changes and in correspondence to the degree of changes, a rough estimation of the number of bacteria causing the caries can be made.

In other words, this invention has the advantages that the structure of the implement is simple, production easy and moreover, mass production possible, thus supply can be made cheaply and the implement will not take up much space due its flat board-like shape, and is a reaction implement as well as a heatable apparatus that can be fixed on to a heated body or heating apparatus, and when application to a heated body or a heating apparatus is done by utilizing human or animal skin, it can be pasted on safely and easily like a plaster, the reacting substance being a laminated material wrapped up inside a film and no measures of environmental pollution is necessary until it is reduced to ashes.

The advantages above will lower the examination expenses in group examination where many people, are examined and screened in a short time and its usefulness is tremendous.

EXAMPLE 2

As another made of the detection implement of this invention, the adhesive sheet was shaped in a square form (FIG. 4) and in a serially linked (FIG. 5) form correspondingly to Example 1.

EXAMPLE 3

As another mode of the detection implement of this invention, the adhesive sheet and protection sheet were made round (FIG. 6) and square (FIG. 7) in the same shape and size and also serially linked (FIG. 8) and made correspondingly to the manner in Example 1.

EXAMPLE 4

Figure 9A:
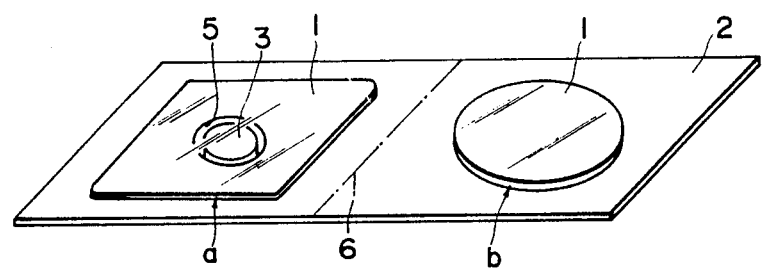
FIGS. 9A, 9B, 10A and 10B show other modes.
Figure 9B:
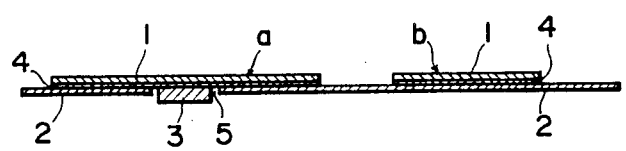

As another mode of the detection implement of this invention, areas "a" and "b" of the adhesive sheet were cut off separately and area "a" was in square and area "b" round (FIGS. 9A and 9B) and made correspondingly to the manner in Example 1.

The detection implement of the invention differs from that disclosed by the drawings in patent application No. 57-106389 in that an opening is made on the protection sheet in advance, and the adhesive surface is shown exposed at this opening, in to where the small test material is placed. Area "b" is made but cut off separately from the same sheet as "a", but as "b" is originally for the purpose to cover the small test material "3" it does not, necessarily have to be a film with an adhesive surface.

EXAMPLE 5

Figure 10A:
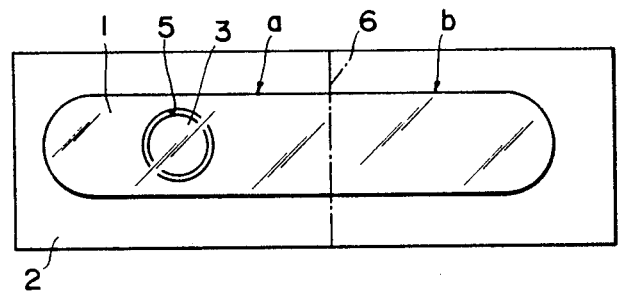
Figure 10B:
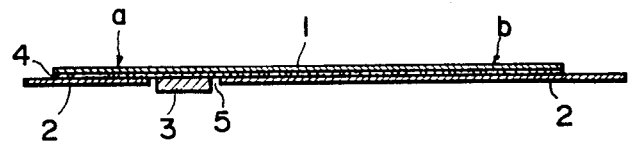

As another mode 7 the detection implement of this invention, the shape of the adhesive sheet was simplified than the various examples mentioned above. Namely, the detection implement in FIGS. 10A and 10B are much simple in shape. The adhesive sheet is a film strip cut round at both ends, which, in its production, will not yield much cutting waste and is thus economical as the adhesion surface to stick to a heated body a heating apparatus will form a crescent mean or a finger mail shape of the thumb at the rounded rim of "a", there will be no adhesive area around the small test material (three facets) like the implements in the other drawings, and even when a simple heated body is used, some sort of a cover is blanketed over said test material to render heating most complete, so the desired purpose can be all attained by having only one adhesion surface as in this drawing.

EXAMPLE 6

Figure 11A:
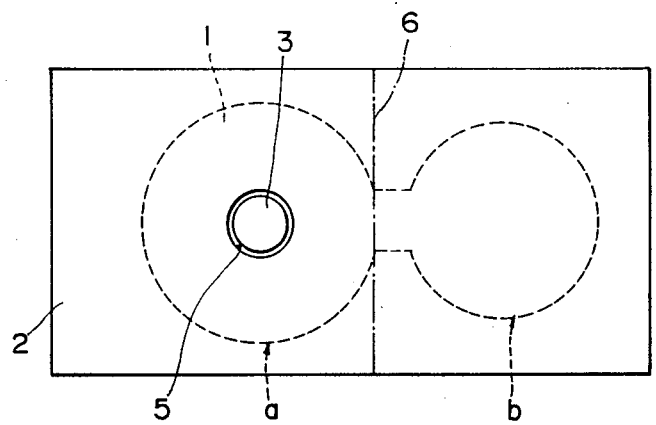
FIGS. 11 A, 11B and 11C are the basic shapes of the detection implement of this invention and respectively represent the plane view, cross-sectional view and the state just before application to a heated body or heating apparatus.
Figure 11B:
Figure 11C:
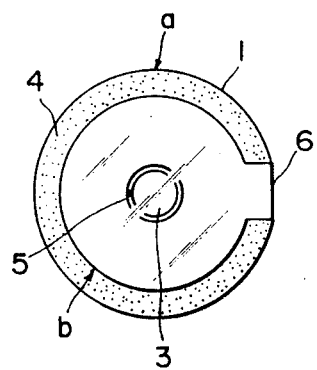

As the basic mode of the detection implement of this invention, implement shown in FIGS. 11A, 11B and 11C and made correspondingly to the manner in Example 1. The "a" and "b" areas of the transparent sheet will form a round shape when laid one over the other.

EXAMPLE 7

In this example, the protection sheet "2" possesses a break portion (or break portions) thereon in order to make ease the separation or peeling off the protection sheet "2" by fingers or finger mails.

We claim:
1. The method of carrying out an analysis of a fluid sample of a substance with a test reagent, the analysis requiring heat from a heat source, said heat source including a part of the human body, which consists of placing an adhesive layer (4) onto one side of an adhesive sheet (1), said adhesive sheet consisting of portion a and portion b, said portion a being larger than portion b, a single folding line located at the intersection of portions a and b, said portion b being transparent, placing a porous test material (3) of size smaller than each of said portions a and b onto said adhesive layer at about the center of said portion a, impregnating said test material with said test reagent, covering the entire surface of said adhesive layer with a peelable protective sheet (2), said protective sheet having an opening (5) of size at least as large as said test material whereby said test material is not in contact with said protective sheet, placing a drop of said fluid sample to be analyzed onto said test material, peeling off said protective sheet, folding said adhesive sheet at said folding line inwardly whereby said portion a overlaps portion b, and forms a folded sheet, said test material then being exposed and then being seen through said portion b, said adhesive layer holding said portions a and b together and a part of portion a protruding beyond portion b to form a protruding part, adhering said protruding part to said heat source whereby said folded sheet containing said test material is heated and the result of the analysis is detected through said transparent portion b.

2. The method according to claim 1 wherein portion a of said adhesive sheet (1), said protection sheet (2) and said test material (3) are transparent or opaque.

3. The method according to claim 1 wherein said adhesive sheet is colored.

4. The method according to claim 1 wherein a plurality of each of test material (3), adhesive layer (4), and adhesive sheet (1) are serially arranged on said protection sheet (2).

5. The method according to claim 1 wherein said portions a and b of said adhesive sheet (1) are made of different material.

6. The method according to claim 1 wherein said protection sheet (2) possesses at least one break portion to facilitate peeling off.

7. The method according to claim 1 wherein said portions a and b are square, round or rectangular.

* * * * *